United States Patent
Anderson

(10) Patent No.: US 6,214,007 B1
(45) Date of Patent: Apr. 10, 2001

(54) SURGICAL FASTENER FOR FIXATION OF A SOFT TISSUE GRAFT TO A BONE TUNNEL

(76) Inventor: David G. Anderson, 68 Apollo Dr., Hampton, VA (US) 23669

( * ) Notice: Subject to any disclaimer, the term of this patent is extended or adjusted under 35 U.S.C. 154(b) by 0 days.

(21) Appl. No.: 09/323,785

(22) Filed: Jun. 1, 1999

(51) Int. Cl.[7] .................................................. A61B 17/56
(52) U.S. Cl. ............................................. 606/73; 606/72
(58) Field of Search .................................. 606/73, 70, 71, 606/72, 74, 104, 60–62, 232; 623/13

(56) References Cited

U.S. PATENT DOCUMENTS

| | | | |
|---|---|---|---|
| 4,708,132 | * 11/1987 | Silvestrini | 128/92 |
| 5,152,790 | * 10/1992 | Rosenberg et al. | 623/13 |

* cited by examiner

Primary Examiner—Michael Buiz
Assistant Examiner—Lien Ngo

(57) ABSTRACT

A surgical fastener and method for attachment of a soft tissue graft to a bone tunnel is disclosed. The surgical fastener comprises a screw and collar. The screw having a conical head and blunt threads. The collar having a conical shape so as to fit over the conical screw head and containing side wall openings. Secure fixation of a soft tissue graft within a bone tunnel may then be achieve by passing the end(s) of the graft through the side wall openings in the collar and then holding tension on the graft while the screw is driven through the collar into the bone tunnel. With seating of the screw head in the collar the soft tissue graft is be firmly held in place as the screw threads and collar compress the graft into the side walls of the tunnel and the graft tails are captured securely by the interface of the screw head and collar. This surgical fastener offers multiple sites of secure graft fixation to avoid slippage of the graft during healing and lies within the bone tunnel so as to avoid being prominent.

5 Claims, 4 Drawing Sheets

SURGICAL FASTENER FOR FIXATION OF A SOFT TISSUE GRAFT TO A BONE TUNNEL

BACKGROUND

1. Field of the Invention

This invention relates to the field of orthopedic surgical fasteners for fixation of a soft tissue grafts to a bone tunnel such as would be required in a knee ligament reconstruction.

2. Description of Prior Art

Reconstruction of torn knee ligaments particularly the anterior cruciate ligament (ACL) and the posterior cruciate ligament (PCL) have become commonplace. Tears of knee ligaments can render the knee unstable leading to recurrent episodes of giving way. Reconstruction of these ligaments by using tendon grafts can result in restoration of knee stability and function. To perform a ligament reconstruction, remnants of the torn ligament are removed. Next, bone tunnels are drilled in the femur and tibia at the attachment site for the ligament to be reconstructed. Next, a tissue graft is spanned between the tunnels with the graft ends buried in the bone tunnels. Finally, the graft is tensioned and attached securely to the bone tunnels. The graft then undergoes a slow process of healing which creates a firm attachment of the graft to bone and establishes a new blood supply for the graft. Over a period of 6–18 months the graft remodels to become living tissue which can resist abnormal motions of the knee that would result in giving way.

The fixation of the graft to bone is of paramount importance as any loosening of the graft can result in failure to restore knee stability. Furthermore, early knee motion and exercises which help the patient to recover quickly from surgery can place significant stress on the graft fixation. Adequate stability of graft fixation must be achieved to allow the patient to safely benefit from the effects of early rehabilitation.

Several types of tissue grafts are available for use in knee ligament reconstruction. Each type of graft has certain advantages and disadvantages. The use of autologous hamstring tendons in knee ligament reconstruction has grown in popularity because this graft causes very minimal morbidity to harvest, does not disrupt the extensor mechanism, creates a very strong soft tissue graft and does not expose a patient to the risks of using cadaver tissue. However, fixation of hamstring grafts to the proximal tibial bone tunnel remains a weak link in successful use of the hamstring tendons. The proximal tibia often contains soft bone providing a weak substrate for implant fixation. A second problem is that the tibia is only covered by a thin layer of soft tissue and a prominent implant can often be palpated beneath the skin causing pain. Other types of soft tissue grafts, both of autologous and cadaver tissue, including achilles tendon, quadriceps tendon, fascia lata and palmaris longus tendon are used in certain situations to reconstruct ligaments and again the weak link of fixation to the bone tunnel remains a problem.

A number of devices are known prior art for fixation of soft tissue grafts to bone. However, as will become evident, each of these devices possesses certain disadvantages that limit their successful use.

The first class of devices for soft tissue to bone fixation includes the suture anchors illustrated by U.S. Pat. No. 5,472,452. In his description, Trott discloses a bone anchor which can be placed in a small bone hole and then serves as the attachment sit for soft tissues which are sutured to the bone. Similar type devices are further disclosed by Lee and Sander in U.S. Pat. No. 5,480,403 and by Hayhurst in U.S. Pat. No. 5,601,557. A variation on this device is disclosed by Ross, Snyder, Marchand in U.S. Pat. No. 5,246,441 where a tack is used to secure soft tissues against the bone as it is driven into a small bone hole. None of these devices would be suitable for fixation of knee ligament grafts because of insufficient holding strength.

A second class of fixation devices is illustrated by U.S. Pat. Nos. 4,454,875 and 4,570,623 where metal staples with spikes on the underside are seen securing ligament tissue to bone. These devices are also undesirable in that they have less than ideal fixation strength. They may also by palpable beneath the skin causing pain and necessitating a second operation for their removal. Finally, these devices are difficult to use and reposition and may cause damage to the bone.

A third class of fixation device is the interference screw. An example of this type of implant is the RCI screw$^R$ marketed by Smith-Nephew Endoscopy Corp. The RCI screw$^R$ has blunt threads to avoid damage to a soft tissue graft. This screw is threaded into a bone tunnel along side the strands of a soft tissue graft. The screw compresses the soft tissue graft against the sides of the bone tunnel. Unfortunately, interference screws have poor fixation strength with soft tissue grafts. In addition, the screw occupies part of the bone tunnel leaving less area for healing.

A forth class of fixation device is the screw-washer combination. This consists of standard bone screws used with a washer which is place distal to the bone tunnel. The screw may be tightened down over a soft tissue graft capturing it against the tibia or can act as an anchor around which to tie sutures. The screw-washer is often prominent causing pain and requiring a second operation for implant removal. Graft fixation is weak leaving concerns of graft slippage.

A fifth class of fixation device is a button over which sutures may be tied. Fixation strength is limited by the strength of the sutures and is poor. In some cases the button may be prominent requiring removal.

Other implants such as the Endobutton® of Smith-Nephew Endoscopy Corp. and various types of threaded pins over which the graft is wrapped are only applicable to fixation of the tendon graft on the femoral side of an ACL reconstruction and thus do not provide a solution to the weak link on the tibial side.

The disadvantages of the available methods of soft tissue fixation can be summarized as:

(a) poor fixation strength allowing slippage of the graft during early rehabilitation;

(b) limited bone to tendon interface for healing;

(c) prominence of the implant which may cause pain;

(d) difficult to adjust fixation;

(e) requirement of second surgery for implant removal;

(f) damage to bone by implant;

(g) implants not amenable to tibia sided graft fixation.

SUMMARY OF THE INVENTION

There is a strong need for an improved method of fixation of soft tissue (tendon) grafts to bone tunnels. An improved surgical fastener and method of fixation are herein disclosed.

The surgical fastener consists of a blunt threaded bone screw with a conical head and a conical shaped collar which fit closely around the head portion of the screw. The collar contains side wall openings to allow the graft strands to pass through and lie between the screw head and collar where they are captured as the screw is tightened.

To use the surgical fastener for ACL reconstruction, the strands of the soft tissue graft are tagged with suture, which is used to apply tension to the graft. Femoral and tibial bone tunnels are then drilled and the opening to the tibial bone tunnel is conically expanded to allow the conical-shaped collar to fit inside the tibial tunnel opening. The soft tissue graft is then pulled through both tunnels and secured to the femoral tunnel by any prior art method. Each strand of the soft tissue graft is placed through a side wall opening of the conical shaped collar so as to pass from outside to inside the collar. The conical shaped collar is then slid over the strands until it is seated in the conical expanded outer opening of the tibial bone tunnel. A screw with a conical shaped head, which has a thread diameter similar to the diameter of the tibial bone tunnel, is selected. Holding tension on the strands of graft, the screw is threaded through the middle of the collar and into the bone tunnel so as to lie in the middle of the graft strand bundle, thus pushing the graft strands into the side walls of the bone tunnel. The screw is seated firmly in the conical-shaped collar so as to capture the graft strands between the head of the screw and the collar and securely compress the strands of graft against the walls of the bone tunnel.

The present surgical fastener contains the following advantages over prior art soft tissue fixation devices:

(a) It provides much more secure fixation of the tendon graft to bone.

(b) It allows early aggressive knee rehabilitation due to fixation strength.

(c) It allows for maximal interface between the tendon graft and bone tunnel to maximize the healing surface area.

(d) It lies within the bone tunnel thus avoiding the problems with graft prominence. This reduces the need for a second operation to remove the implant.

(e) It is easily adjustable allowing for intra-operative modification of tendon graft tensioning if necessary.

(f) It stabilizes the graft throughout the bone tunnel preventing graft motion within the bone tunnel which can delay healing and erode bone.

(g) It uniformly compresses the graft against the bone tunnel side walls thus stimulating quicker healing and revascularization of the soft tissue graft.

(h) It can be used with a variety of soft tissue grafts.

(i) It provides for multiple areas of fixation of a soft tissue graft thus relieving high stress concentration on a specific point which can lead to graft failure.

(j) It is easy to manufacture and use.

Further objects and advantages will become apparent with consideration of the following description and drawings.

DRAWING FIGURES

Figure 3A:
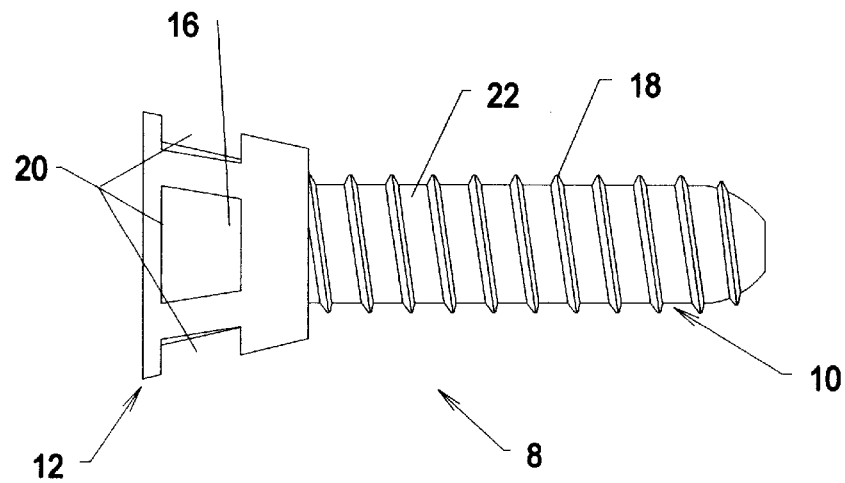
Figure 3B:
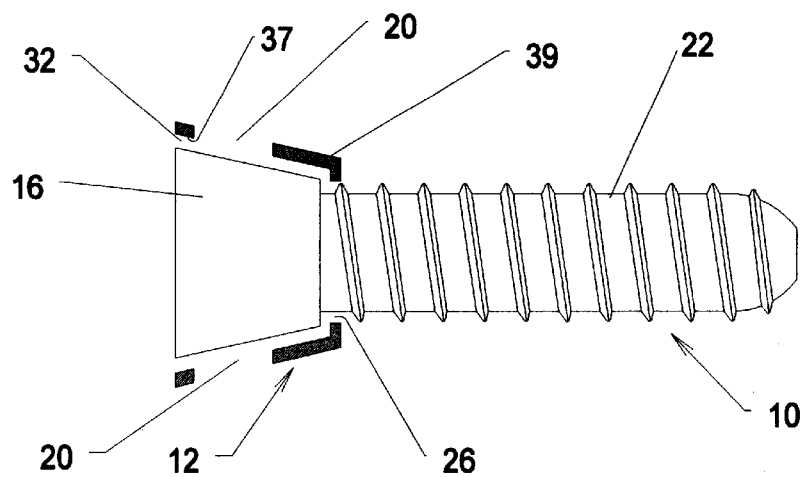
Figure 3C:
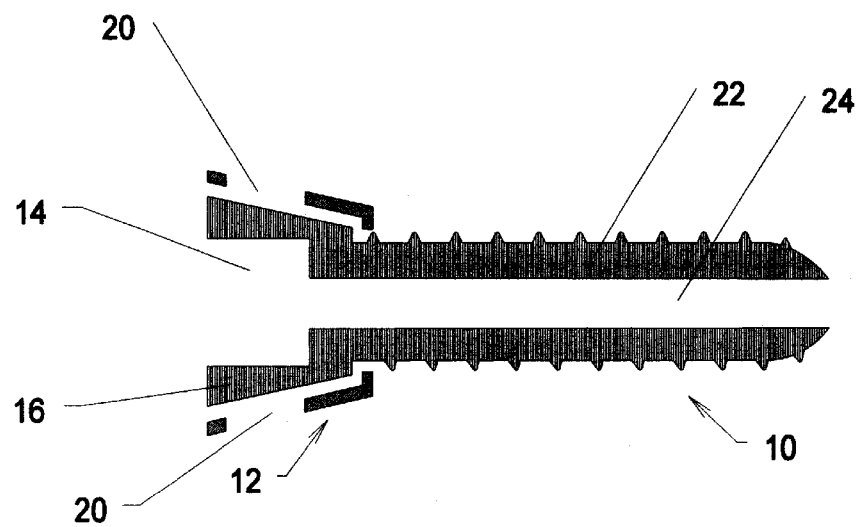

FIGS. 3A–C shows side views of the screw and overfitting collar. 3A shows the screw and collar from a side view. 3B shows the collar in cross-section while the screw remains in side view. 3C shows both the screw and collar in cross-section.

Figure 4:
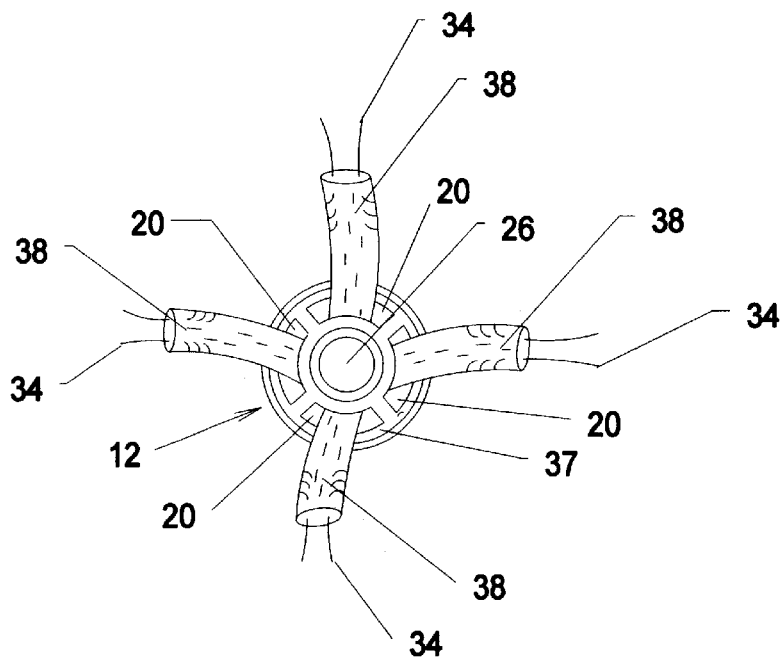

FIG. 4 shows an end-on view of the collar with four tendon strands projecting through the side wall passages in the collar.

Figure 5:
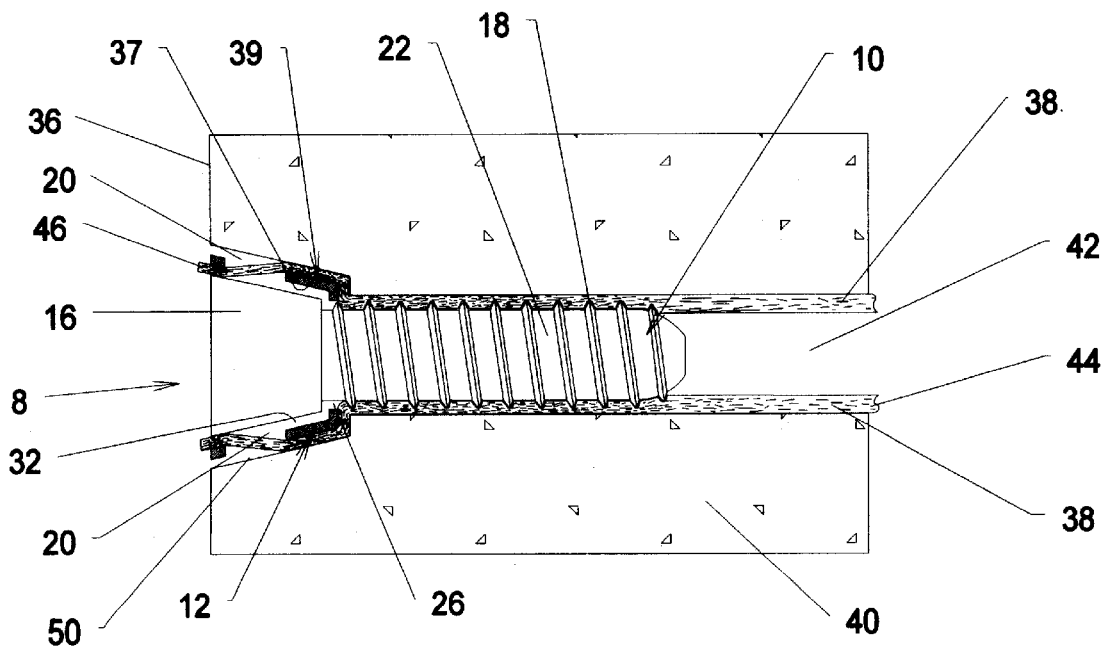

FIG. 5 shows the cross section of the screw and collar stabilizing a soft tissue graft within a bone tunnel. The screw is seen from a side view while the tunnel, graft and collar are show in cross section to demonstrate their function.

Figure 6:
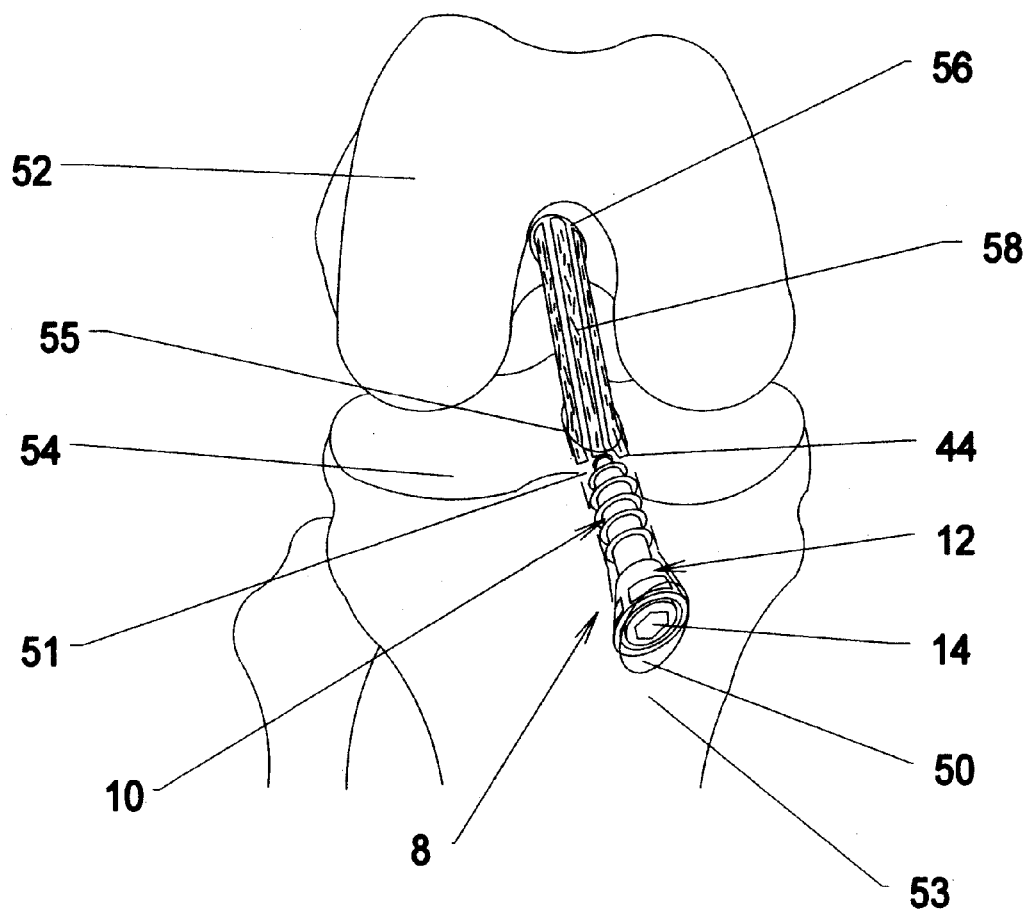

FIG. 6 shows a view of a knee joint with a soft tissue ACL reconstruction. The surgical fastener can be seen in the tibial bone tunnel through the transparent tibia. The soft tissue graft is interruped in the tibial tunnel to allow the surgical fastener to be seen.

| Referenece Numerals in Drawings | |
|---|---|
| 10 screw | 32 space between screw head and collar |
| 12 collar | 34 suture tags |
| 14 screw driver socket | 36 outer surface of bone |
| 16 conical screw head | 37 inner surface of collar |
| 18 blunt threads | 38 soft tissue graft strand |
| 20 side wall openings | 39 outer surface of collar |
| 22 screw shank | 40 bone |
| 24 cannulation passage | 42 bone tunnel |
| 26 central collar openmg | 44 graft interrupted |
| 30 conical side walls | 46 capture site |
| 50 conical expanded opening | 54 tibia |
| 51 tibial bone tunnel | 56 femoral bone tunnel |
| 52 femur | 58 multi-stranded ACL graft |
| 53 outer surface of the tibia | |

DESCRIPTION—FIGS. 1–6

Figure 1:
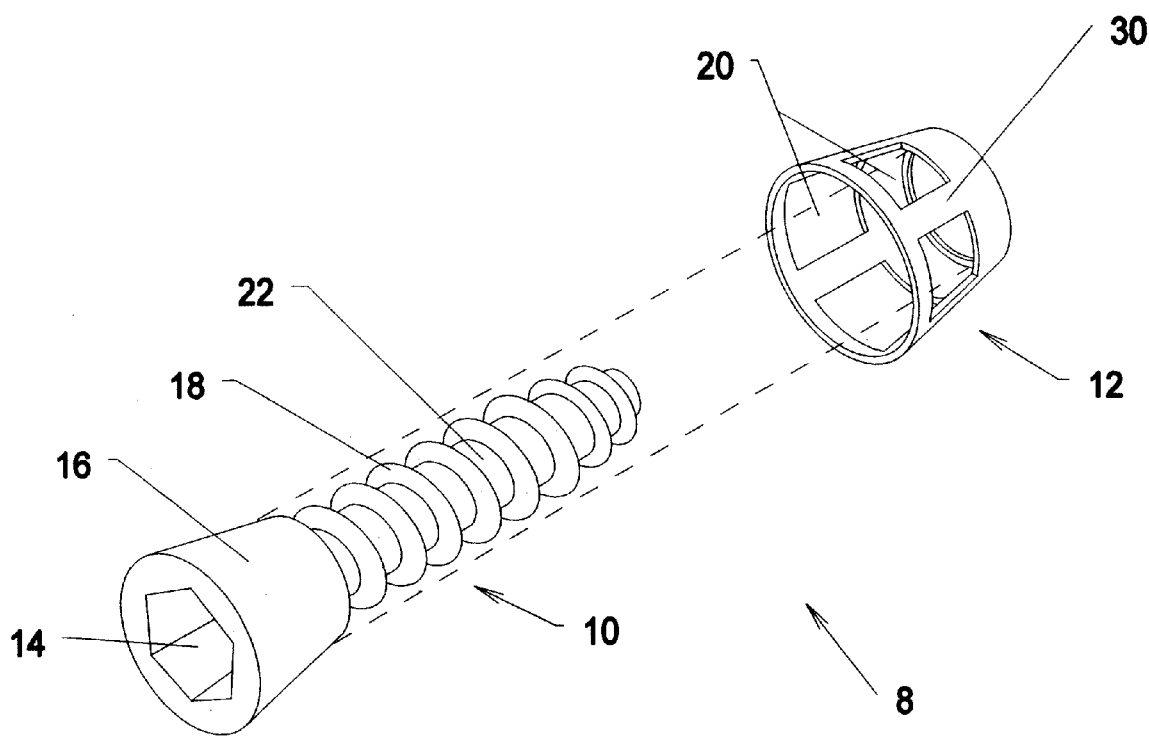
FIG. 1 shows an exploded view of the screw and collar.
Figure 2:
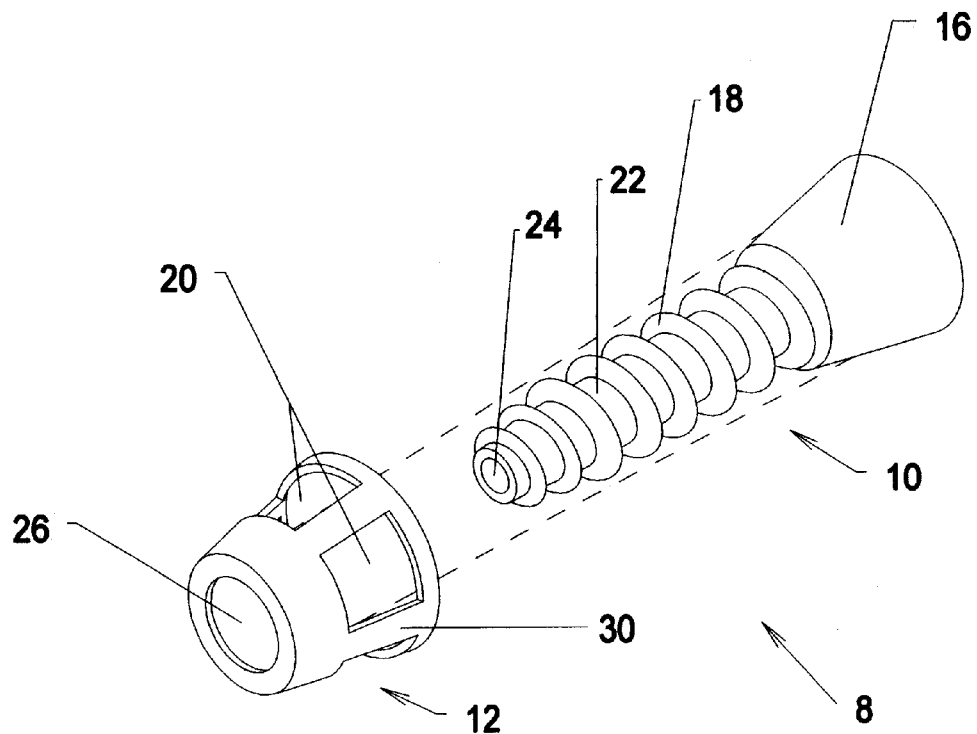
FIG. 2 shows as exploded view of the screw and collar from a second perspective.

An exploded view of the implant is seen from two different perspectives in FIGS. 1 & 2. The surgical fastener 8 comprises two components a screw 10 and a collar 12. The collar 12 is conical in shape and fits over the screw head 16, which has a similar conical shape. The collar 12 has conical side walls 30 with side wall openings 20 and a central passage 26. The side wall openings 20 allow passage of the strands of a soft tissue graft while the central passage 26 allows the passage of the screw shank 22. The screw 10 has a conical screw head 16, which contains a screwdriver socket 14 that may be used to manipulate the screw with a screwdriver. The screw shank 22 has blunt threads 18. These blunt threads 18 have smooth, rounded edges so as to prevent cutting of a soft tissue graft. FIG. 2 shows a cannulation passage 24, which passes through the center of the screw 10 so that the screw 10 may be introduced over a guide wire.

FIG. 3A shows a side view of the surgical fastener 8 comprising the screw 10 and the overfitting collar 12. The screw 10 has been placed into the collar 12 so that the collar 12 is overfitting the screw head 16 which may still be partially seen through the side wall openings 20. The screw shank 22 has blunt threads 18. FIG. 3B shows the collar 12 in cross section while the screw 10 is seen from a side view. The collar 12 fits over the screw head 16 with only a small space between the screw head and collar 32. The collar 12 has an outer surface 39 and an inner surface 37, which lies adjacent to the screw head 16. Side wall openings 20 connect the outer surface 39 of the collar with the space between the screw head and collar 32. The central collar opening 26 allows the passage of the screw shank 22. FIG. 3C shows both the screw 10 and collar 12 in cross section. The screw head 16 contains a screwdriver socket 14 for manipulation of the screw 10 with a screwdriver. A cannulation passage 24 passes through the middle of the screw shank 22 to allow the screw 10 to be introduced over a guide wire.

FIG. 4 shows a view looking into the large end of the collar 12. Four soft tissue graft strands 38 are seen passing through the side wall openings 20 of the collar 12. Each of the soft tissue graft strands 38 contains a suture tag 34, which is used to apply tension to the soft tissue graft strands 38. The soft tissue graft strands 38 pass through the side wall openings 20 and lie against the inner surface 37 of the collar 12. The central passage 26 directs the screw 10 (FIGS. 1–3) between the soft tissue graft strands 38, which may be captured against the inner surface 37 of the collar.

FIG. 5 shows the surgical fastener 8 securing soft tissue graft strands 38 within a bone tunnel 42. The screw 10 is seen from a side view while the collar 12, soft tissue grafts strands 38 and bone tunnel 42 are seen in cross-section. The bone 40 contains a bone tunnel 42 that has a conical expanded opening 50. The collar 12 is seated within the conical expanded opening 50. The screw 10 is seated within the bone tunnel 42 and collar 12 such that the screw head 16 lies in close approximation to the collar 12. The soft tissue graft strands 38 pass through the periphery of the bone tunnel 42 along the shank 22 of the screw 10 and into the conical expanded opening 50. There, the soft tissue graft strands 38 passes along the outside surface of the collar 39, through the side wall openings 20, to the space between the screw head and collar 32. The soft tissue graft strands 38 are compressed between the screw head 16 and the inner surface 37 of the collar 12 at the capture site 46. The soft tissue grafts strands 38 are also compressed against the sides of the bone tunnel 42 by the screw shank 22. The surgical fastener 8 is flush with the outer surface of the bone 36. By pressing the soft tissue graft strands 38 against the periphery of the bone tunnel 42, the area for healing of the graft is maximized.

FIG. 6 shows a preferred embodiment of the invention—using the surgical fastener 8 for fixation of the tibial side of a soft tissue graft during ACL reconstruction. The knee joint comprises the ends of the femur 52 and tibia 54. Within the knee, a multi-stranded ACL graft 58 spans the knee joint from the femoral bone tunnel 56 to the tibial bone tunnel 51. The surgical fastener 8 is in place within the tibial bone tunnel 51 and can be seen transparently through the bone of the tibia 54. The multi-stranded ACL graft 58 has been interrupted 44 at the edge of the surgical fastener 8 in this diagram to allow the fastener 8 to be seen. The tibial bone tunnel 51 extends from the opening inside the knee 55 to the conical expanded opening 50 at the outer surface of the tibia 53. The conical expanded opening 50 allows the collar 12 and screw 10 to seat completely within the tibial bone tunnel 51 so that the surgical fastener 8 is not palpable beneath the skin causing pain to the patient. The screw 10 contains a screwdriver socket 14, which allows the screw to be threadably inserted through the collar 12 and into the tibial bone tunnel 51.

OPERATION—FIGS. 4–6

The operation of the surgical fastener 8 can be easily understood by considering the previously described FIGS. 4–6. The descriptions will pertain specifically to the preferred embodiment using the surgical fastener 8 to secure a multi-stranded ACL graft to the tibial tunnel 51 as seen in FIG. 6. However, this should not be seen as limiting the scope of this invention as other uses for this surgical fastener are conceived.

To use the surgical fastener 8 to secure the tibial aspect of a multi-stranded ACL graft 58 begin by performing the standard surgical setup, preparation and arthroscopic examination as routinely performed during arthroscopically assisted reconstruction of the ACL. Proceed using standard techniques to remove the old ACL scar tissue and widen the femoral notch if needed. The tibial and femoral bone tunnels would be placed in the standard locations and drilled with standard techniques except that the tibial tunnel should be prepared with a conical expanded opening 50. Preparation of the conical expanded opening 50 of the tibial tunnel 51 (FIG. 6) could easily be performed by techniques well known to the art, for example, by use of a conical shaped drill or reamer. A soft tissue graft, for example, the hamstring tendons of the gracilis and semitendinosis muscles would be obtained by standard techniques and prepared by placing tag sutures 34 in the ends of the tendon grafts 38 (FIG. 4). By doubling these two tendons over, a four-strand soft tissue graft is obtained. The multi-stranded ACL graft 58 would then be delivered into the knee by standard techniques, for example, by using a cable device that pulls the graft into the knee as the ends of the cable are pulled taught. The femoral side of the ACL graft would be secured by standard techniques, for example, by use of a smooth pin that passes through the middle of the graft within the femoral tunnel. Note that the technique of ACL reconstruction to this point consists of well-known, prior art techniques. The ends of the soft tissue graft strands 38 would now protrude from the conical expanded opening 50 of the tibial bone tunnel 51 (FIGS. 5,6). Each soft tissue graft strand 38 should now be passed through an individual side wall opening 20 in the collar 12 as seen in FIGS. 4&5. The strands 38 pass from outside to inside the collar 12 so that the soft tissue graft strand 38 bundle is contained inside the large end of the conical collar 12. Holding the soft tissue graft strands 38 securely by the suture tags 34, the collar 12 should be pushed along the soft tissue grafts strands 38 until the collar 12 is completely seated within the conical expanded opening 50 of the tibial bone tunnel 51 (FIG. 6). Next, a screw 10 with a shank 22 diameter that is similar to the bone tunnel 42 should be passed through the central passage 26 of the collar 12 and threaded into the bone tunnel 42 (FIG. 5). While seating the screw 10 it is important to hold manual tension on the suture tags 34 so that the graft will be taught when the screw 10 seats into the collar 12 securing the soft tissue graft strands 38 in place. Once the screw 10 is seated within the collar 12, the knee can be tested for stability and the incisions may be sutured closed by standard techniques.

If needed, the screw may be introduced over a guide wire. The purpose of the guide wire is to direct the path of the screw 10 along the course of the guide wire. To use a guide wire, the ACL reconstruction is performed using standard techniques as outlined above to the point of securing the tibial side of the soft tissue graft. The soft tissue graft strands 38 are passed through the side wall openings 20 of the collar 12 from outside to inside. The collar 12 is slid over the soft tissue graft strands 38 until it is seated in the conical expanded opening 50 of the bone tunnel 42 (FIG. 5) as described above. Next, a guide wire is placed into the central passage 26 of the collar 12 between the soft tissue graft strands 38. A screw 10 with a shank 22 diameter similar to the bone tunnel 42 is placed onto the guide wire by directing the guide wire into the cannulation passage 24 (FIG. 3c) of the screw 10. The diameter of the guide wire should be slightly smaller than the diameter of the cannulation passage 24 to allow the screw 10 to rotate around the axis of the guide wire. The screw 10 may then be threaded through the central passage 26 of collar 12 and into the tibial bone tunnel 51 (FIG. 6) while holding tension on the suture tags 34 (FIG. 4). The screw 10 is threaded until it is completely seated into the collar 12 and the soft tissue graft strands 38 are secured (FIG. 5). The guide wire is then pulled out of the cannulation passage 24.

To remove the surgical fastener 8, the screw 10 is unthreaded from the bone tunnel 42 using a screwdriver. The collar 12 is then grasped, for example, with a standard surgical clamp and removed from the conical expanded opening 50 allowing the tendon grafts 38 to slide out of the side wall passages 20 (FIG. 5).

In manufacturing this surgical fastener 8, the number of side wall passages 20 may be varied to accommodate grafts with different numbers of strands. The collar 12 and screw 10 can be manufactured in sizes to accommodate a wide range of patients. Also, the cannulation passage 24 is optional depending on the preferences of the surgeon using the device. Different material may be use for manufacture of the fastener including stainless steel, titanium alloy, cobalt chromium alloy, polyethylene and the bioabsorbable materials including polymers of lactide, glycolide, caprolactone, polydioxanone, trimethylene carbonate, polyorthoesters, polyethelene oxide or blends of the above polymers.

What is claimed:

1. A surgical fastener for securing a soft tissue graft to a bone tunnel, which comprises:
   a) a screw having a threaded portion and a conical shaped head portion; said head portion containing a means for threadable insertion of said screw;
   b) a collar comprising a conical shape with one or more side wall passages and a central passage; said conical shape being substantially similar to said head portion of said screw so as to over fit said head portion of said screw; said side wall passages being intended for the passage of strands of a soft tissue graft; said central passage being intended for the passage of said threaded portion of said screw;
   c) a means of forming a conical expanded opening to said bone tunnel which is substantially similar to said collar, so as to allow said collar to fit within said conical expanded opening;
   d) a means of introducing said strands of said soft tissue graft through said side wall passages of said collar;
   e) a means of slidably introducing said collar over said soft tissue graft strands until said collar is seated in said conical expanded opening to said bone tunnel;
   f) a means of inserting said threaded portion of said screw through said central passage in said collar and threadably introducing said screw into said bone tunnel so as to securely capture said soft tissue graft between said head portion and said collar;
   g) a means of compressing said soft tissue graft into said bone tunnel so as to promote healing of said soft tissue graft;
   whereby tensile stresses in said secured soft tissue graft are resisted.

2. The surgical fastener of claim 1 wherein said surgical fastener is used to achieve fixation of the tibial side of a soft tissue graft during anterior cruciate ligament reconstruction surgery.

3. The surgical fastener of claim 1 whereby said screw has blunt threads so as to prevent damage to said soft tissue graft.

4. The surgical fastener of claim 1 whereby said screw contains a central cannulation passage such that it may be introduced over a guide wire.

5. The surgical fastener of claim 1 being made of materials selected from a group consisting of stainless steel, titanium alloy, cobalt chromium alloy, polyethelene, or polymers of lactide, glycolide, caprolactone, polydioxanone, trimethylene carbonate, polyesters, polyethylene oxide or blends of the above polymers.

* * * * *